United States Patent
Chen et al.

(10) Patent No.: US 11,559,374 B2
(45) Date of Patent: *Jan. 24, 2023

(54) RELEASE AGENT RECEPTACLE

(71) Applicant: Align Technology, Inc., San Jose, CA (US)

(72) Inventors: Jennifer C. Chen, San Francisco, CA (US); Li-Hung Su, Foster City, CA (US); Chunhua Li, Cupertino, CA (US)

(73) Assignee: Align Technology, Inc., San Jose, CA (US)

( * ) Notice: Subject to any disclaimer, the term of this patent is extended or adjusted under 35 U.S.C. 154(b) by 14 days.

This patent is subject to a terminal disclaimer.

(21) Appl. No.: 16/223,019

(22) Filed: Dec. 17, 2018

(65) Prior Publication Data

US 2019/0231483 A1 Aug. 1, 2019

Related U.S. Application Data

(63) Continuation of application No. 14/863,059, filed on Sep. 23, 2015, now Pat. No. 10,154,889, which is a continuation of application No. 14/558,418, filed on Dec. 2, 2014, now Pat. No. 9,730,769, which is a continuation of application No. 12/011,942, filed on
(Continued)

(51) Int. Cl.
| | |
|---|---|
| *A61C 7/08* | (2006.01) |
| *A61C 19/06* | (2006.01) |
| *A61C 7/00* | (2006.01) |
| *A61K 49/00* | (2006.01) |
| *A61C 19/04* | (2006.01) |

(52) U.S. Cl.
CPC .............. *A61C 7/08* (2013.01); *A61C 7/00* (2013.01); *A61C 19/063* (2013.01); *A61C 19/066* (2013.01); *A61K 49/00* (2013.01); *A61C 19/04* (2013.01)

(58) Field of Classification Search
CPC .............................. A61C 7/08; A61B 71/085
See application file for complete search history.

(56) References Cited

U.S. PATENT DOCUMENTS

| | | |
|---|---|---|
| 2,467,432 A | 4/1949 | Kesling |
| 2,835,628 A | 5/1958 | Saffir |
| (Continued) | | |

FOREIGN PATENT DOCUMENTS

| | | |
|---|---|---|
| CN | 1867317 A | 11/2006 |
| DE | 4123352 A1 | 1/1993 |
| (Continued) | | |

OTHER PUBLICATIONS

Partial International Search Report from international application No. PCT/US2008/005680, dated Aug. 18, 2008, 5 pp.
(Continued)

*Primary Examiner* — Ralph A Lewis
(74) *Attorney, Agent, or Firm* — Shay Glenn LLP

(57) ABSTRACT

The present disclosure includes method, system, apparatus, and indicator embodiments. One apparatus includes an appliance for placement over one or more teeth and a release agent receptacle including an outer portion provided on appliance surface, an inner portion provided within the outer portion, and one or more apertures formed in the outer portion.

19 Claims, 5 Drawing Sheets

Related U.S. Application Data

Jan. 29, 2008, now Pat. No. 8,899,976, which is a continuation-in-part of application No. 11/799,979, filed on May 3, 2007, now Pat. No. 7,854,609, which is a continuation-in-part of application No. 10/949,717, filed on Sep. 24, 2004, now Pat. No. 7,553,157.

(56) References Cited

U.S. PATENT DOCUMENTS

| | | |
|---|---|---|
| 3,192,302 A | 6/1965 | Keefer |
| 3,407,500 A | 10/1968 | Kesling |
| 3,503,127 A | 3/1970 | Kasdin et al. |
| 3,533,163 A | 10/1970 | Kirschbaum |
| 3,555,386 A | 1/1971 | Wisman |
| 3,564,205 A | 2/1971 | Tyler |
| 3,600,808 A | 8/1971 | Reeve |
| 3,660,900 A | 5/1972 | Andrews |
| 3,665,770 A | 5/1972 | Sagi et al. |
| 3,683,502 A | 8/1972 | Wallshein |
| 3,704,985 A | 12/1972 | Pickett et al. |
| 3,733,905 A | 5/1973 | Bremer |
| 3,813,781 A * | 6/1974 | Forgione ............... A61F 5/566 433/68 |
| 3,848,335 A | 11/1974 | Bergersen |
| 3,860,803 A | 1/1975 | Levine |
| 3,885,310 A | 5/1975 | Northcutt |
| 3,916,526 A | 11/1975 | Schudy |
| 3,922,786 A | 12/1975 | Lavin |
| 3,950,851 A | 4/1976 | Bergersen |
| 3,968,690 A | 7/1976 | Blouin et al. |
| 3,991,178 A | 11/1976 | Humbert et al. |
| 4,014,096 A | 3/1977 | Dellinger |
| 4,039,653 A | 8/1977 | DeFoney et al. |
| 4,044,762 A | 8/1977 | Jacobs |
| 4,072,268 A | 2/1978 | Perris |
| 4,124,793 A | 11/1978 | Colman |
| 4,192,456 A | 3/1980 | Shields et al. |
| 4,195,046 A | 3/1980 | Kesling |
| 4,253,828 A | 3/1981 | Coles et al. |
| 4,255,138 A | 3/1981 | Frohn |
| 4,278,087 A | 7/1981 | Theeuwes |
| 4,310,047 A | 1/1982 | Branson |
| 4,324,546 A | 4/1982 | Heitlinger et al. |
| 4,324,547 A | 4/1982 | Arcan et al. |
| 4,348,178 A | 9/1982 | Kurz |
| 4,447,164 A | 5/1984 | Berndt |
| 4,450,150 A | 5/1984 | Sidman |
| 4,478,580 A | 10/1984 | Barrut |
| 4,500,294 A | 2/1985 | Lewis |
| 4,505,673 A | 3/1985 | Yoshii |
| 4,526,540 A | 7/1985 | Dellinger |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,629,424 A | 12/1986 | Lauks et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,713,243 A | 12/1987 | Schiraldi et al. |
| 4,741,700 A | 5/1988 | Barabe |
| 4,755,139 A | 7/1988 | Abbatte et al. |
| 4,763,791 A | 8/1988 | Halverson et al. |
| 4,768,951 A | 9/1988 | Abiru et al. |
| 4,793,803 A | 12/1988 | Martz |
| 4,798,534 A | 1/1989 | Breads |
| 4,818,542 A | 4/1989 | De Luca et al. |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,861,268 A | 8/1989 | Garay et al. |
| 4,877,398 A | 10/1989 | Kesling |
| 4,880,380 A | 11/1989 | Martz |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,968,251 A | 11/1990 | Darnell |
| 4,975,052 A | 12/1990 | Spencer et al. |
| 4,983,334 A | 1/1991 | Adell |
| 4,990,089 A | 2/1991 | Munro |
| 4,997,369 A | 3/1991 | Shafir |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,049,077 A | 9/1991 | Goldin et al. |
| 5,055,039 A | 10/1991 | Abbatte et al. |
| 5,074,786 A | 12/1991 | Woodward |
| 5,076,791 A | 12/1991 | Madray |
| 5,085,585 A | 2/1992 | Zimble |
| 5,100,316 A | 3/1992 | Wildman |
| 5,121,333 A | 6/1992 | Riley et al. |
| 5,127,903 A | 7/1992 | Mailot et al. |
| 5,128,870 A | 7/1992 | Erdman et al. |
| 5,131,843 A | 7/1992 | Hilgers et al. |
| 5,131,844 A | 7/1992 | Marinaccio et al. |
| 5,137,449 A | 8/1992 | Goldin et al. |
| 5,139,419 A | 8/1992 | Andreiko et al. |
| 5,145,364 A | 9/1992 | Martz et al. |
| 5,165,424 A | 11/1992 | Silverman |
| 5,194,003 A | 3/1993 | Garay et al. |
| 5,219,625 A | 6/1993 | Matsunami et al. |
| 5,236,355 A * | 8/1993 | Brizzolara ............ A61K 9/1647 433/80 |
| 5,273,429 A | 12/1993 | Rekow et al. |
| 5,278,756 A | 1/1994 | Lemchen et al. |
| 5,326,685 A | 7/1994 | Gaglio et al. |
| 5,338,198 A | 8/1994 | Wu et al. |
| 5,340,309 A | 8/1994 | Robertson |
| 5,342,202 A | 8/1994 | Deshayes |
| 5,367,478 A | 11/1994 | Hattori |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,437,872 A | 8/1995 | Lee |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,575,654 A | 11/1996 | Fontenot |
| 5,575,655 A | 11/1996 | Darnell |
| 5,587,520 A | 12/1996 | Rhodes |
| 5,587,912 A | 12/1996 | Andersson et al. |
| 5,605,459 A | 2/1997 | Kuroda et al. |
| 5,607,305 A | 3/1997 | Andersson et al. |
| 5,645,420 A * | 7/1997 | Bergersen ............... A61C 7/08 433/6 |
| 5,645,421 A | 7/1997 | Slootsky |
| 5,651,671 A | 7/1997 | Seay et al. |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,740,267 A | 4/1998 | Echerer et al. |
| 5,800,174 A | 9/1998 | Andersson |
| 5,842,860 A * | 12/1998 | Funt ..................... A61J 7/0092 433/80 |
| 5,846,058 A | 12/1998 | Fischer |
| 5,866,058 A | 2/1999 | Batchelder et al. |
| 5,879,158 A | 3/1999 | Doyle et al. |
| 5,880,961 A | 3/1999 | Crump |
| 5,911,576 A | 6/1999 | Ulrich et al. |

(56) References Cited

U.S. PATENT DOCUMENTS

| | | | |
|---|---|---|---|
| 5,924,863 A | 7/1999 | Jacobs et al. | |
| 5,957,686 A | 9/1999 | Anthony | |
| 5,964,587 A | 10/1999 | Sato | |
| 5,971,754 A | 10/1999 | Sondhi et al. | |
| 5,975,893 A | 11/1999 | Chishti et al. | |
| 5,980,246 A | 11/1999 | Ramsay et al. | |
| 5,993,413 A | 11/1999 | Aaltonen et al. | |
| 6,044,309 A | 3/2000 | Honda | |
| 6,049,743 A | 4/2000 | Baba | |
| 6,068,475 A | 5/2000 | Stoyka | |
| 6,089,869 A | 7/2000 | Schwartz | |
| 6,099,303 A | 8/2000 | Gibbs et al. | |
| 6,123,544 A | 9/2000 | Cleary | |
| 6,142,780 A | 11/2000 | Burgio | |
| 6,159,498 A | 12/2000 | Tapolsky et al. | |
| 6,183,248 B1 | 2/2001 | Chishti et al. | |
| 6,190,165 B1 | 2/2001 | Andreiko et al. | |
| 6,217,334 B1 | 4/2001 | Hultgren | |
| 6,274,122 B1 | 8/2001 | McLaughlin | |
| 6,293,790 B1 | 9/2001 | Hilliard | |
| 6,309,215 B1 | 10/2001 | Phan et al. | |
| 6,457,801 B1* | 10/2002 | Fish | B41J 29/393 347/19 |
| 6,491,037 B1 | 12/2002 | Mortenson | |
| 6,551,579 B2 | 4/2003 | Sagel et al. | |
| 6,607,382 B1* | 8/2003 | Kuo | A61C 7/08 433/6 |
| 6,813,131 B2 | 11/2004 | Schmalz | |
| 6,814,085 B2 | 11/2004 | Brattesani et al. | |
| 6,935,572 B1 | 8/2005 | Smole | |
| 7,194,781 B1 | 3/2007 | Orjela | |
| 7,553,157 B2* | 6/2009 | Abolfathi | A61C 7/00 433/6 |
| 7,824,180 B2 | 11/2010 | Abolfathi et al. | |
| 7,854,609 B2* | 12/2010 | Chen | A61C 7/00 433/6 |
| 7,878,801 B2* | 2/2011 | Abolfathi | A61C 7/00 433/6 |
| 7,905,724 B2 | 3/2011 | Kuo et al. | |
| 8,771,149 B2 | 7/2014 | Rahman et al. | |
| 8,899,976 B2 | 12/2014 | Chen | |
| 9,730,769 B2 | 8/2017 | Chen | |
| 10,154,889 B2* | 12/2018 | Chen | A61C 7/00 |
| 2003/0008259 A1* | 1/2003 | Kuo | A61C 7/08 433/6 |
| 2003/0211440 A1 | 11/2003 | Kuo et al. | |
| 2004/0005277 A1* | 1/2004 | Willison | A61C 19/063 424/53 |
| 2006/0068353 A1 | 3/2006 | Abolfathi et al. | |
| 2006/0115782 A1 | 6/2006 | Li et al. | |
| 2006/0115785 A1 | 6/2006 | Li et al. | |
| 2007/0207434 A1 | 9/2007 | Kuo et al. | |
| 2008/0118882 A1 | 5/2008 | Su | |

FOREIGN PATENT DOCUMENTS

| | | |
|---|---|---|
| EP | 490848 A2 | 6/1992 |
| EP | 541500 A1 | 5/1993 |
| EP | 774933 B1 | 12/2000 |
| EP | 731673 B1 | 5/2001 |
| FR | 2369828 A1 | 6/1978 |
| GB | 529805 A | 11/1940 |
| GB | 710764 A | 6/1954 |
| GB | 761565 A | 11/1956 |
| GB | 905213 A | 9/1962 |
| GB | 1274283 A | 5/1972 |
| GB | 2279876 A | 1/1995 |
| WO | WO91/004713 A1 | 4/1991 |
| WO | WO94/010935 A1 | 5/1994 |
| WO | WO98/032394 A1 | 7/1998 |
| WO | WO98/044865 A1 | 10/1998 |
| WO | 1998058596 A1 | 12/1998 |
| WO | WO98/055079 A2 | 12/1998 |
| WO | WO02/024100 A1 | 3/2002 |
| WO | 02058583 A1 | 8/2002 |
| WO | 2005114183 A1 | 12/2005 |
| WO | 2006060547 A2 | 6/2006 |
| WO | WO2008/137069 A2 | 11/2008 |

OTHER PUBLICATIONS

Benson et al., "Highly Porous Polymers," American Laboratory, pp. 1-12, Apr. 2003.

Brannon-Peppas, "Biomaterials: Polymers in Controlled Drug Delivery," Medical Devicelink, Medical Plastics and Biomaterials Magazine, 19 pp., Nov. 1997.

Landgraf et al., "Polymer Microcarrier Exhibiting Zero-Order Release," Drug Delivery Technology, vol. 3, No. 1, pp. 1-14, 2003.

Lawrence, "Salivary Markers of Systemic Disease," Journal of Canadian Dental Association Clinical Practice, vol. 68, No. 3., pp. 170-174, Mar. 2002.

Middleton et al., "Materials: Synthetic Biodegradable Polymers as Medical Devices," Medical Plastics and Biomaterials Magazine, MPB Article Index, 14 pp., 1998.

Nishanian et al., "Oral Fluids as an Alternative to Serum for Measurement of Markers of Immune Activation," Clinical and Diagnostic Laboratory Immunology, vol. 5, No. 4, pp. 507-512, Jul. 1998.

Sigma-Aldrich Co., "Tutorial, Biocompatible/Biodegradable Materials," http://www.sigmaaldrich.com/area_of_interest/organic_inorganic_chemistry/materials_science/biocompatible_, undated, 3 pp.

Svec et al., "Molded Rigid Monolithic Porous Polymers: An Inexpensive, Efficient, and Versatile Alternative to Beads for the Design of Materials for Numerous Applications," Ind. Eng. Chem. Res. 1999, 38, pp. 34-48.

Unknown, Excerpt from a reference on water-soluble polymers, date unknown, 2 pp.

Van Der Eijk et al., "Paired measurements of quantitative hepatitis B virus DNA in saliva and serum of chronic hepatitis B patients: implications for saliva as infectious agent," Journal of Clinical Virology, vol. 29, pp. 92-94, 2004.

Extended Search Report from related European Patent Application No. 16191809, dated Feb. 10, 2017, 7 pp.

First Office Action from related Chinese patent application No. 201410060043, dated Dec. 21, 2015, 6 pp.

AADR. American Association for Dental Research; Summary of Activities; Los Angeles, CA; p. 195; Mar. 20-23,(year of pub. sufficiently earlier than effective US filing date and any foreign priority date) 1980.

Alexander et al.; The DigiGraph Work Station Part 2 Clinical Management; J. Clin. Orthod.; pp. 402-407; (Author Manuscript); Jul. 1990.

Altschuler et al.; Analysis of 3-D Data for Comparative 3-D Serial Growth Pattern Studies of Oral-Facial Structures; AADR Abstracts, Program and Abstracts of Papers, 57th General Session, IADR Annual Session, Mar. 29, 1979-Apr. 1, 1979, New Orleans Marriot; Journal of Dental Research; vol. 58, Special Issue A, p. 221; Jan. 1979.

Altschuler et al.; Laser Electro-Optic System for Rapid Three-Dimensional (3D) Topographic Mapping of Surfaces; Optical Engineering; 20(6); pp. 953-961; Dec. 1981.

Altschuler et al.; Measuring Surfaces Space-Coded by a Laser-Projected Dot Matrix; SPIE Imaging q Applications for Automated Industrial Inspection and Assembly; vol. 182; pp. 187-191; Oct. 10, 1979.

Altschuler; 3D Mapping of Maxillo-Facial Prosthesis; AADR Abstract #607; 2 pages total, (year of pub. sufficiently earlier than effective US filing date and any foreign priority date) 1980.

Andersson et al.; Clinical Results with Titanium Crowns Fabricated with Machine Duplication and Spark Erosion; Acta Odontologica Scandinavica; 47(5); pp. 279-286; Oct. 1989.

Andrews, The Six Keys to Optimal Occlusion Straight Wire, Chapter 3, L.A. Wells; pp. 13-24; (year of pub. sufficiently earlier than effective US filing date and any foreign priority date) 1989.

(56) References Cited

OTHER PUBLICATIONS

Baumrind et al., "Mapping the Skull in 3-D," reprinted from J. Calif. Dent. Assoc, 48(2), 11 pages; (year of pub. sufficiently earlier than effective US filing date and any foreign priority date) Fall Issue 1972.

Baumrind et al.; A Stereophotogrammetric System for the Detection of Prosthesis Loosening in Total Hip Arthroplasty; NATO Symposium on Applications of Human Biostereometrics; SPIE; vol. 166; pp. 112-123; Jul. 9-13, 1978.

Baumrind; A System for Cranio facial Mapping Through the Integration of Data from Stereo X-Ray Films and Stereo Photographs; an invited paper submitted to the 1975 American Society of Photogram Symposium on Close-Range Photogram Systems; University of Illinois; pp. 142-166; Aug. 26-30, 1975.

Baumrind; Integrated three-dimensional craniofacial mapping: background, principles, and persectives; Seminars in Orthodontics; 7(4); pp. 223-232; Dec. 2001.

Baumrind; Integrated Three-Dimensional Craniofacial Mapping: Background, Principles, and Perspectives; Seminars in Orthodontics; 7(4); pp. 223-232; Dec. 2001.

Begole et al.; A Computer System for the Analysis of Dental Casts; The Angle Orthodontist; 51(3); pp. 252-258; Jul. 1981.

Bernard et al.; Computerized Diagnosis in Orthodontics for Epidemiological Studies: A ProgressReport; (Abstract Only), J. Dental Res. Special Issue, vol. 67, p. 169, paper presented at International Association for Dental Research 66th General Session, Montreal Canada; Mar. 9-13, 1988.

Bhatia et al.; A Computer-Aided Design for Orthognathic Surgery; British Journal of Oral and Maxillofacial Surgery; 22(4); pp. 237-253; Aug. 1, 1984.

Biggerstaff et al.; Computerized Analysis of Occlusion in the Postcanine Dentition; American Journal of Orthodontics; 61(3); pp. 245-254; Mar. 1972.

Biggerstaff; Computerized Diagnostic Setups and Simulations; Angle Orthodontist; 40(1); pp. 28-36; Jan. 1970.

Biostar Operation & Training Manual. Great Lakes Orthodontics, Ltd. 199 Fire Tower Drive,Tonawanda, New York. 14150-5890, 20 pages; (year of pub. sufficiently earlier than effective US filing date and any foreign priority date) 1990.

Brandestini et al.; Computer Machined Ceramic Inlays: In Vitro Marginal Adaptation; J. Dent. Res. Special Issue; (Abstract 305); vol. 64; p. 208; (year of pub. sufficiently earlier than effective US filing date and any foreign priority date) 1985.

Brook et al.; An Image Analysis System for the Determination of Tooth Dimensions from Study Casts: Comparison with Manual Measurements of Mesio-distal Diameter; Journal of Dental Research; 65(3); pp. 428-431; Mar. 1986.

Burstone et al.; Precision Adjustment of the Transpalatal Lingual Arch: Computer Arch Form Predetermination; American Journal of Orthodontics; 79(2);pp. 115-133; Feb. 1981.

Burstone; Dr. Charles J. Burstone on The Uses of the Computer in Orthodontic Practice (Part 1); Journal of Clinical Orthodontics; 13(7); pp. 442-453; (interview); Jul. 1979.

Cardinal Industrial Finishes; Powder Coatings; 6 pages; retrieved from the internet (http://www.cardinaipaint.com) on Aug. 25, 2000.

Chaconas et al,; The DigiGraph Work Station, Part 1, Basic Concepts; Journal of Clinical Orthodontics; 24(6); pp. 360-367; (Author Manuscript); Jun. 1990.

Chafetz et al.; Subsidence of the Femoral Prosthesis, A Stereophotogrammetric Evaluation; Clinical Orthopaedics and Related Research; No. 201; pp. 60-67; Dec. 1985.

Chiappone; Constructing the Gnathologic Setup and Positioner; Journal of Clinical Orthodontics; 14(2); pp. 121-133; Feb. 1980.

Chishti et al.; U.S. Appl. No. 60/050,342 entitled "Procedure for moving teeth using a seires of retainers," filed Jun. 20, 1997.

Cottingham; Gnathologic Clear Plastic Positioner; American Journal of Orthodontics; 55(1); pp. 23-31; Jan. 1969.

Crawford; CAD/CAM in the Dental Office: Does It Work?; Canadian Dental Journal; 57(2); pp. 121-123 Feb. 1991.

Crawford; Computers in Dentistry: Part 1: CAD/CAM: The Computer Moves Chairside, Part 2: F. Duret' A Man With A Vision, Part 3; The Computer Gives New Vision- Literally, Part 4: Bytes 'N Bites The Computer Moves From The Front Desk To The Operatory; Canadian Dental Journal; 54(9); pp. 661-666 Sep. 1988.

Crooks; CAD/CAM Comes to USC; USC Dentistry; pp. 14-17; (year of pub. sufficiently earlier than effective US filing date and any foreign priority date) Spring 1990.

Cureton; Correcting Malaligned Mandibular Incisors with Removable Retainers; Journal of Clinical Orthodontics; 30(7); pp. 390-395; Jul. 1996.

Curry et al.; Integrated Three-Dimensional Craniofacial Mapping at the Craniofacial Research InstrumentationLaboratory/University of the Pacific; Seminars in Orthodontics; 7(4); pp. 258-265; Dec. 2001.

Cutting et al.; Three-Dimensional Computer-Assisted Design of Craniofacial Surgical Procedures; Optimization and Interaction with Cephalometric and CT-Based Models; Plastic and Reconstructive Surgery; 77(6); pp. 877-885; Jun. 1986.

DCS Dental AG; The CAD/CAM 'DCS Titan System' for Production of Crowns/Bridges; DSC Production; pp. 1-7; Jan. 1992.

Defranco et al.; Three-Dimensional Large Displacement Analysis of Orthodontic Appliances; Journal of Biomechanics; 9(12); pp. 793-801; Jan. 1976.

Dental Institute University of Zurich Switzerland; Program for International Symposium on Computer Restorations: State of the Art of the CEREC-Method; 2 pages; May 1991.

Dentrac Corporation; Dentrac document; pp. 4-13; (year of pub. sufficiently earlier than effective US filing date and any foreign priority date) 1992.

DENT-X; Dentsim . . . Dent-x's virtual reality 3-D training simulator . . . A revolution in dental education; 6 pages; retrieved from the internet (http://www.dent-x.com/DentSim.htm); on Sep. 24, 1998.

Duret et al.; CAD/CAM Imaging in Dentistry; Current Opinion in Dentistry; 1(2); pp. 150-154; Apr. 1991.

Duret et al.; CAD-CAM in Dentistry; Journal of the American Dental Association; 117(6); pp. 715-720; Nov. 1988.

Duret; The Dental CAD/CAM, General Description of the Project; Hennson International Product Brochure, 18 pages; Jan. 1986.

Duret; Vers Une Prosthese Informatisee; Tonus; 75(15); pp. 55-57; (English translation attached); 23 pages; Nov. 15, 1985.

Economides; The Microcomputer in the Orthodontic Office; Journal of Clinical Orthodontics; 13(11); pp. 767-772; Nov. 1979.

Elsasser; Some Observations on the History and Uses of the Kesling Positioner; American Journal of Orthodontics; 36(5); pp. 368-374; May 1, 1950.

Faber et al.; Computerized Interactive Orthodontic Treatment Planning; American Journal of Orthodontics; 73(1); pp. 36-46; Jan. 1978.

Felton et al.; A Computerized Analysis of the Shape and Stability of Mandibular Arch Form; American Journal of Orthodontics and Dentofacial Orthopedics; 92(6); pp. 478-483; Dec. 1987.

Friede et al.; Accuracy of Cephalometric Prediction in Orthognathic Surgery; Journal of Oral and Maxillofacial Surgery; 45(9); pp. 754-760; Sep. 1987.

GIM-ALLDENT Deutschland, "Das DUX System: Die Technik," 3 pages; (English Translation Included); (year of pub. sufficiently earlier than effective US filing date and any foreign priority date); 2002.

Grayson; New Methods for Three Dimensional Analysis of Craniofacial Deformity, Symposium: Computerized Facial Imaging in Oral and Maxillofacial Surgery; American Association of Oral and Maxillofacial Surgeons; 48(8) suppl 1; pp. 5-6; Sep. 13, 1990.

Guess et al.; Computer Treatment Estimates In Orthodontics and Orthognathic Surgery; Journal of Clinical Orthodontics; 23(4); pp. 262-268; 11 pages; (Author Manuscript); Apr. 1989.

Heaven et al.; Computer-Based Image Analysis of Artificial Root Surface Caries; Abstracts of Papers #2094; Journal of Dental Research; 70:528; (Abstract Only); Apr. 17-21, 1991.

Hoffmann et al.; Role of Cephalometry for Planning of Jaw Orthopedics and Jaw Surgery Procedures; Informatbnen, pp. 375-396; (English Abstract Included); Mar. 1991.

(56) References Cited

OTHER PUBLICATIONS

Huckins; CAD-CAM Generated Mandibular Model Prototype from MRI Data; AAOMS, p. 96; (Abstract Only); (year of pub. sufficiently earlier than effective US filing date and any foreign priority date) 1999.
Jablonski; Illustrated dictionary of dentistry, W.B. Saunders Company; ISBN 0-7216-5055-4; pp. 678-680; copyright 1982.
JCO Interviews; Craig Andreiko, DDS, MS on the Elan and Orthos Systems; Interview by Dr. Larry W. White; Journal of Clinical Orthodontics; 28(8); pp. 459-468; 14 pages; (Author Manuscript); Aug. 1994.
JCO Interviews; Dr. Homer W. Phillips on Computers in Orthodontic Practice, Part 2; Journal of Clinical Orthodontics; 17(12); pp. 819-831; 19 pages; (Author Manuscript); Dec. 1983.
Jerrold; The Problem, Electronic Data Transmission and the Law; American Journal of Orthodontics and Dentofacial Orthopedics; 113(4); pp. 478-479; 5 pages; (Author Manuscript); Apr. 1998.
Jones et al.; An Assessment of the Fit of a Parabolic Curve to Pre- and Post-Treatment Dental Arches; British Journal of Orthodontics; 16(2); pp. 85-93; May 1989.
Kamada et.al.; Case Reports On Tooth Positioners Using LTV Vinyl Silicone Rubber; J. Nihon University School of Dentistry; 26(1); pp. 11-29; (year of pub. sufficiently earlier than effective US filing date and any foreign priority date) 1984.
Kamada et.al.; Construction of Tooth Positioners with LTV Vinyl Silicone Rubber and Some Case KJ Reports; J. Nihon University School of Dentistry; 24(1); pp. 1-27; (year of pub. sufficiently earlier than effective US filing date and any foreign priority date) 1982.
Kanazawa et al.; Three-Dimensional Measurements of the Occlusal Surfaces of Upper Molars in a Dutch Population; Journal of Dental Research; 63(11); pp. 1298-1301; Nov. 1984.
Kesling et al.; The Philosophy of the Tooth Positioning Appliance; American Journal of Orthodontics and Oral surgery; 31(6); pp. 297-304; Jun. 1945.
Kesling; Coordinating the Predetermined Pattern and Tooth Positioner with Conventional Treatment; American Journal of Orthodontics and Oral Surgery; 32(5); pp. 285-293; May 1946.
Kleeman et al.; The Speed Positioner; J. Clin. Orthod.; 30(12); pp. 673-680; Dec. 1996.
Kunii et al.; Articulation Simulation for an Intelligent Dental Care System; Displays; 15(3); pp. 181-188; Jul. 1994.
Kuroda et al.; Three-Dimensional Dental Cast Analyzing System Using Laser Scanning; American Journal of Orthodontics and Dentofacial Orthopedics; 110(4); pp. 365-369; Oct. 1996.
Laurendeau et al.; A Computer-Vision Technique for the Acquisition and Processing of 3-D Profiles of 7 Dental Imprints: An Application in Orthodontics; IEEE Transactions on Medical Imaging; 10(3); pp. 453-461; Sep. 1991.
Lleinfelder et al.; A New Method for Generating Ceramic Restorations: a CAD-CAM System; Journal of the American Dental Association; 118(6); pp. 703-707; Jun. 1989.
McCann; Inside the ADA; J. Amer. Dent. Assoc, 118:286-294; Mar. 1989.
McNamara et al.; Invisible Retainers; J. Clin Orthod.; pp. 570-578; 11 pages; (Author Manuscript); Aug. 1985.
McNamara et al.; Orthodontic and Orthopedic Treatment in the Mixed Dentition; Needham Press; pp. 347-353; Jan. 1993.
Moermann et al., Computer Machined Adhesive Porcelain Inlays: Margin Adaptation after Fatigue Stress; IADR Abstract 339; J. Dent. Res.; 66(a):763; (Abstract Only); (year of pub. sufficiently earlier than effective US filing date and any foreign priority date) 1987.
Mormann et al.; Marginale Adaptation von adhasuven Porzellaninlays in vitro; Separatdruck aus:Schweiz. Mschr. Zahnmed.; 95; pp. 1118-1129; 8 pages; (Machine Translated English Abstract); (year of pub. sufficiently earlier than effective US filing date and any foreign priority date); 1985.
Nahoum; The Vacuum Formed Dental Contour Appliance; N. Y. State Dent. J.; 30(9); pp. 385-390; Nov. 1964.

Nash; Cerec CAD/CAM Inlays: Aesthetics and Durability in a Single Appointment; Dentistry Today; 9(8); pp. 20, 22-23 and 54; Oct. 1990.
Nishiyama et al.; A New Construction of Tooth Repositioner by LTV Vinyl Silicone Rubber; The Journal of Nihon University School of Dentistry; 19(2); pp. 93-102 (year of pub. sufficiently earlier than effective US filing date and any foreign priority date) 1977.
Pinkham; Foolish Concept Propels Technology; Dentist, 3 pages, Jan./Feb. 1989.
Pinkham; Inventor's CAD/CAM May Transform Dentistry; Dentist; pp. 1 and 35, Sep. 1990.
Ponitz; Invisible retainers; Am. J. Orthod.; 59(3); pp. 266-272; Mar. 1971.
Procera Research Projects; Procera Research Projects 1993 ' Abstract Collection; 23 pages; (year of pub. sufficiently earlier than effective US filing date and any foreign priority date) 1993.
Proffit et al.; The first stage of comprehensive treatment: alignment and leveling; Contemporary Orthodontics; (Second Ed.); Chapter 15, MosbyYear Book; St. Louis, Missouri; pp. 470-533 Oct. 1993.
Raintree Essix & Ars Materials, Inc., Raintree Essix, Technical Magazine Table of contents and Essix Appliances, 7 pages; retrieved from the internet (http://www.essix.com/magazine/defaulthtml) on Aug. 13, 1997.
Rekow; A Review of the Developments in Dental CAD/CAM Systems; Current Opinion in Dentistry; 2; pp. 25-33; Jun. 1992.
Rekow; CAD/CAM in Dentistry: A Historical Perspective and View of the Future; Journal Canadian Dental Association; 58(4); pp. 283, 287-288; Apr. 1992.
Rekow; Computer-Aided Design and Manufacturing in Dentistry: A Review of the State of the Art: Journal of Prosthetic Dentistry; 58(4); pp. 512-516; Dec. 1987.
Rekow; Dental CAD-CAM Systems: What is the State of the Art?; The Journal of the American Dental Association; 122(12); pp. 43-48; Dec. 1991.
Rekow; Feasibility of an Automated System for Production of Dental Restorations, Ph.D. Thesis; Univ. of Minnesota, 250 pages, Nov. 1988.
Richmond et al.; The Development of the PAR Index (Peer Assessment Rating): Reliability and Validity.; The European Journal of Orthodontics; 14(2); pp. 125-139; Apr. 1992.
Richmond et al.; The Development of a 3D Cast Analysis System; British Journal of Orthodontics; 13(1); pp. 53-54; Jan. 1986.
Richmond; Recording The Dental Cast In Three Dimensions; American Journal of Orthodontics and Dentofacial Orthopedics; 92(3); pp. 199-206; Sep. 1987.
Rudge; Dental Arch Analysis: Arch Form, A Review of the Literature; The European Journal of Orthodontics; 3(4); pp. 279-284; Jan. 1981.
Sakuda et al.; Integrated Information-Processing System In Clinical Orthodontics: An Approach with Use of a Computer Network System; American Journal of Orthodontics and Dentofacial Orthopedics: 101(3); pp. 210-220; 20 pages; (Author Manuscript) Mar. 1992.
Savage; A preliminary report into the development and use of soluble controlled-release glass timing discs implanted into orthodontic appliances; British Journal of Orthodontics; 9(4); pp. 190-193; Oct. 9, 1982.
Schellhas et al.; Three-Dimensional Computed Tomography in Maxillofacial Surgical Planning; Archives of Otolaryngology—Head and Neck Surgery; 114(4); pp. 438-442; Apr. 1988.
Schroeder et al; Eds. The Visual Toolkit, Prentice Hall PTR, New Jersey; Chapters 6, 8 & 9, (pp. 153-210,309-354, and 355-428; (year of pub. sufficiently earlier than effective US filing date and any foreign priority date) 1998.
Segu et al.; Computer-aided cefalometry and new mechanics in orthodontics; Fortschr. Kieferothop; 44; pp. 370-376; (English Abstract);Sep. 1983.
Shilliday; Minimizing finishing problems with the mini-positioner; American Journal of Orthodontics; 59(6); pp. 596-599; Jun. 1971.

(56) References Cited

OTHER PUBLICATIONS

Siemens; CEREC—Computer-Reconstruction, High Tech in der Zahnmedizin; 15 pagesl; (Includes Machine Translation); (year of pub. sufficiently earlier than effective US filing date and any foreign priority date); 2004.
Sirona Dental Systems GmbH, CEREC 3D, Manuel utiiisateur, Version 2.0X (in French); 114 pages; (English translation of table of contents included); (year of pub. sufficiently earlier than effective US filing date and any foreign priority date); 2003.
Stoll et al.; Computer-aided Technologies in Dentistry; Dtsch Zahna'rztl Z 45, pp. 314-322; (English Abstract Included); (year of pub. sufficiently earlier than effective US filing date and any foreign priority date) 1990.
U.S. Department of Commerce, National Technical Information Service, Holodontography: An Introduction to Dental Laser Holography; School of Aerospace Medicine Brooks AFB Tex; Mar. 1973, 40 pages; Mar. 1973.
U.S. Department of Commerce, National Technical Information Service; Automated Crown Replication Using Solid Photography SM; Solid Photography Inc., Melville NY,; 20 pages; Oct. 1977.
Van Der Linden et al.; Three-Dimensional Analysis of Dental Casts by Means of the Optocom; Journal of Dental Research; 51(4); p. 1100; Jul.-Aug. 1972.
Van Der Linden; A New Method to Determine Tooth Positions and Dental Arch Dimensions; Journal of Dental Research; 51(4); p. 1104; Jul.-Aug. 1972.
Van Der Zel; Ceramic-Fused-to-Metal Restorations with a New CAD/CAM System; Quintessence International; 24(A); pp. 769-778; (year of pub. sufficiently earlier than effective US filing date and any foreign priority date); 1993.
Varady et al.; Reverse Engineering Of Geometric Models'An Introduction; Computer-Aided Design; 29(4); pp. 255-268; 20 pages; (Author Manuscript); Apr. 1997.
Warunek et al.; Physical and Mechanical Properties of Elastomers in Orthodonic Positioners; American Journal of Orthodontics and Dentofacial Orthopedics; 95(5); pp. 388-400; 21 pages; (Author Manuscript); May 1989.
Warunek et.al.; Clinical Use of Silicone Elastomer Applicances; JCO; 23(10); pp. 694-700; Oct. 1989.
Wells; Appiication of the Positioner Appliance in Orthodontic Treatment; American Journal of Orthodontics; 58(4); pp. 351-366; Oct. 1970.
Williams; Dentistry and CAD/CAM: Another French Revolution; J. Dent. Practice Admin.; 4(1); pp. 2-5 Jan./Mar. 1987.
Williams; The Switzerland and Minnesota Developments in CAD/CAM; Journal of Dental Practice Administration; 4(2); pp. 50-55; Apr./Jun. 1987.
Wishan; New Advances in Personal Computer Applications for Cephalometric Analysis, Growth Prediction, Surgical Treatment Planning and Imaging Processing; Symposium: Computerized Facial Imaging in Oral and Maxilofacial Surgery: p. 5; Presented on Sep. 13, 1990.
Yamamoto et al.; Optical Measurement of Dental Cast Profile and Application to Analysis of Three-Dimensional Tooth Movement in Orthodontics; Front. Med. Biol. Eng., 1(2); pp. 119-130; (year of pub. sufficiently earlier than effective US filing date and any foreign priority date); 1988.
Yamamoto et al.; Three-Dimensional Measurement of Dental Cast Profiles and Its Applications to Orthodontics; Conf. Proc. IEEE Eng. Med. Biol. Soc.; 12(5); pp. 2052-2053; Nov. 1990.
Yoshii; Research on a New Orthodontic Appliance: The Dynamic Positioner (D.P.); 111. The General Concept of the D.P. Method and Its Therapeutic Effect, Part 1, Dental and Functional Reversed Occlusion Case Reports: Nippon Dental Review; 457; pp. 146-164; 43 pages; (Author Manuscript); Nov. 1980.
Yoshii; Research on a New Orthodontic Appliance: The Dynamic Positioner (D.P.); I. The D.P. Concept and Implementation of Transparent Silicone Resin (Orthocon); Nippon Dental Review; 452; pp. 61-74; 32 pages; (Author Manuscript); Jun. 1980.
Yoshii; Research on a New Orthodontic Appliance: The Dynamic Positioner (D.P.); II. The D.P. Manufacturing Procedure and Clinical Applications; Nippon Dental Review; 454; pp. 107-130; 48 pages; (Author Manuscript); Aug. 1980.
Yoshii; Research on a New Orthodontic Appliance: The Dynamic Positioner (D.P.); III- The General Concept of the D.P. Method and Its Therapeutic Effect. Part 2. Skeletal Reversed Occlusion Case Reports; Nippon Dental Review; 458; pp. 112-129; 40 pages; (Author Manuscript); Dec. 1980.
U.S. Food and Drug Administration: Color additives; 3 pages; retrieved from the internet (https://websrchive.org/web/20070502213911/http://www.cfsan.fda.gov/~dms/col-toc.html); last known as May 2, 2007.
Yamany et al.; A System for Human Jaw Modeling Using Intra-Orai Images; Proc. of the 20th Annual Conf. of the IEEE Engineering in Medicine and Biology Society; vol. 2; pp. 563-566; Oct. 1998.

* cited by examiner

RELEASE AGENT RECEPTACLE

RELATED APPLICATIONS

The present application is a continuation of U.S. patent application Ser. No. 14/863,059, filed Sep. 23, 2015, which is a continuation of U.S. patent application Ser. No. 14/558,418, filed Dec. 2, 2014, now U.S. Pat. No. 9,730,769 on Aug. 15, 2017, which is a continuation of U.S. patent application Ser. No. 12/011,942, filed Jan. 29, 2008, now U.S. Pat. No. 8,899,976 on Dec. 2, 2014, which is a continuation in part (CIP) of U.S. patent application Ser. No. 11/799,979, filed May 3, 2007, now U.S. Pat. No. 7,854,609, which was a continuation in part (CIP) of U.S. patent application Ser. No. 10/949,717, filed on Sep. 24, 2004, now U.S. Pat. No. 7,553,157, the disclosure of which is incorporated in its entirety herein by reference.

BACKGROUND

The present disclosure is related to systems and methods for providing release agent receptacles.

As noted in commonly owned U.S. Pat. No. 6,607,382 entitled "Methods and systems for concurrent tooth repositioning and substance delivery," the content of which is incorporated herewith, the repositioning of teeth may be accomplished with the use of a series of removable elastic positioning appliances such as the Invisalign® system available from Align Technology, Inc., the assignee of the present disclosure. Such appliances have a thin shell of elastic material that generally conforms to a patient's teeth but is slightly out of alignment with an initial or immediately prior tooth configuration. Placement of the elastic positioner over the teeth applies controlled forces in specific locations to gradually move the teeth into the new configuration. Repetition of this process with successive appliances including new configurations eventually moves the teeth through a series of intermediate configurations or alignment patterns to a final desired configuration. A full description of an exemplary elastic polymeric positioning appliance is described in U.S. Pat. No. 5,975,893, and in published PCT application WO 98/58596, the content of these documents are incorporated by reference for all purposes.

The appliance is effective in repositioning teeth when it is placed over the patient's teeth. In some implementations, it is desirable to wear these appliances most of the day (e.g., all of the time except when eating and maintaining oral hygiene, such as by brushing or flossing). Although easy and convenient to wear, the patient may not wear the appliance as prescribed by the treatment professional. Extended removal of the appliance, for any reason beyond what is recommended, interrupts the treatment plan and lengthens the overall period of treatment. Since the appliance is removable by the patient, the treatment professional has to rely on the patient to comply with the prescription.

Additionally, there may be many variables and differences in each patient's oral environment and, therefore, one type of compliance indicator may not likely be enough to last for a desired period of wear in every person. Some examples of the factors that may change the wear rate include an amount of saliva produced, one or more tooth anatomies or locations, a composition of saliva, an analysis of sleep habits of a patient, an amount of liquid consumption, and one or more types of liquid consumed, among other criteria. These factors can make the analysis of compliance based upon a wear indicator difficult due to the different wear rates that different people may have.

SUMMARY

The present disclosure includes method, system, apparatus, and indicator embodiments. One apparatus includes an appliance for placement over one or more teeth and a release agent receptacle including an outer portion provided on appliance surface, an inner portion provided within the outer portion, and one or more apertures formed in the outer portion.

Another apparatus embodiment includes an apparatus for monitoring orthodontic treatment compliance includes an appliance adapted to be worn over one or more teeth; and a compliance indicator mounted on the appliance or teeth to indicate compliance. Advantages of some embodiments of the system include one or more of the following. Some such apparatus embodiments provide better data for communicating device compliance with patients, including: increased patient knowledge and recall of appliance usage; increased compliance in wearing the dental appliance, and increased patient satisfaction as a result. The apparatus provides a channel of self-monitoring for the patient. The apparatus also reduces patient's anxiety levels without requiring verbal or written instructions since device usage is self-evident. The treatment professional also has better information on patient progress during the treatment.

DESCRIPTION

Figure 1:
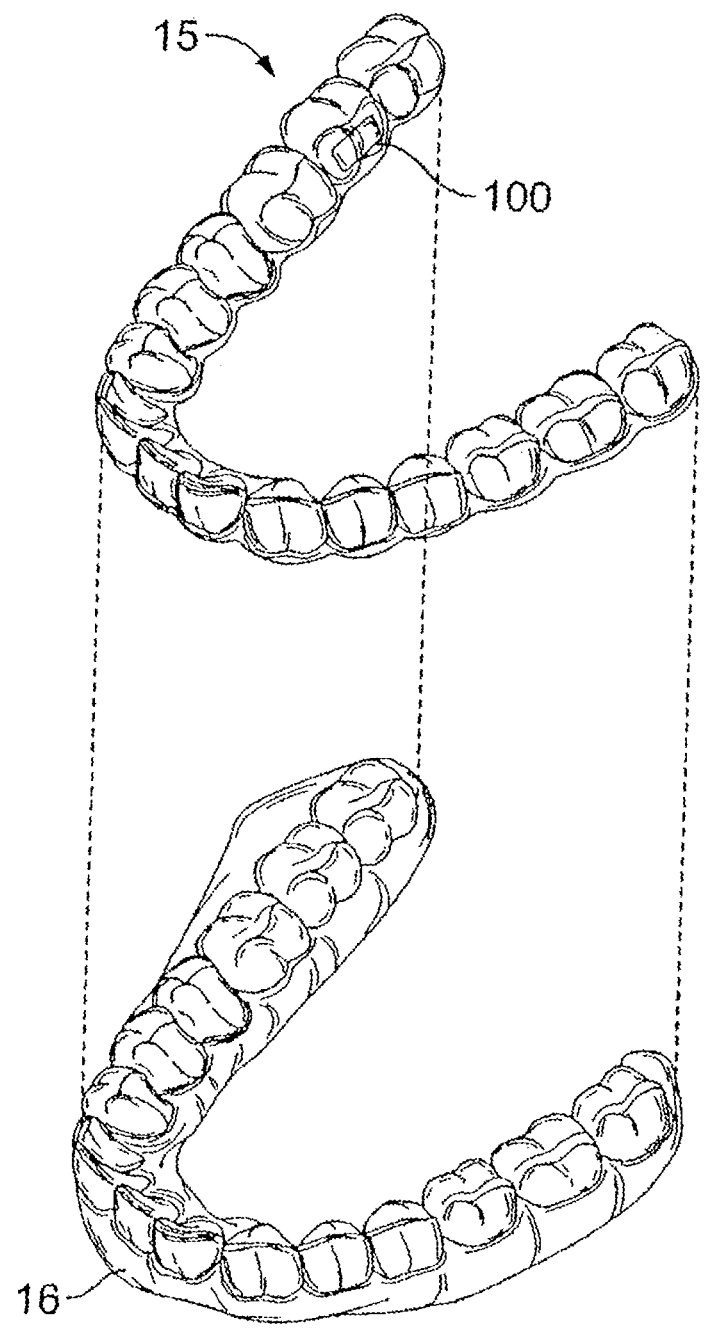
FIG. 1 shows an exemplary compliance indicator.

FIG. 1 shows an exemplary removable appliance 15 adapted to fit over teeth on a jaw 16. A usage indicator 100 can be mounted on one tooth or on the appliance 15 to indicate patient compliance.

In one implementation, the indicator 100 can be a coat on a tooth or an appliance with a chemical agent. Alternatively, the indicator 100 can be an electrical agent, optical agent or mechanical agent that indicates appliance wearage. In some embodiments, the indicator agent is inactive until contact with liquid or moisture. Alternatively, release of the agent can be stimulated by liquid or moisture. Thus, in one case, upon wearing, oral fluids activates the agent and allows the agent to seep out and indicate compliance. Alternatively, oral fluids such as saliva, among others, can seep in to activate the agent to indicate compliance.

In another embodiment, the appliance can release a coloring agent to the oral environment when the appliance is worn over the teeth. Such mechanisms may include a layer which includes the agent. The layer may be formed over at least a portion of the surfaces of the repositioning appliance. These surfaces include both the cavity surfaces, the surfaces within the cavities which contact the teeth when in place, and the external surfaces, the surfaces of the appliance which contact the cheeks and lips when in place. The layer may be of various materials and may take a variety of forms. For example, the layer may consist essentially of the agent. In other words, the agent may be attached directly to a surface of the polymer shell of an elastic repositioning appliance. This may be achieved by applying the agent (optionally in an inert carrier or diluent) itself to the surface utilizing a number of methods, such as spraying, painting and/or dipping. When the repositioning appliance is placed over the patient's teeth, the agent may then be released to the oral environment.

Alternatively, the layer may include the agent present in or on a carrier or binder which promotes adhesion or attachment to the appliance and/or which creates a matrix from which the agent can be released by diffusion or dissolution. In some embodiments, the agent is dissolved in the carrier or binder. In this case, the agent may be provided in powder or similar form and dissolved in a liquid solvent. The result may be a solution which may be applied to a surface of the shell, typically by spraying, painting, and/or dipping, to form a coating or film. When the repositioning appliance is placed over the patient's teeth, the compliance indicating agent may then be released from the coating to the oral environment. Release may be due to activation or deactivation of the carrier or any other releasing mechanism, such as by enzymes or proteins in oral fluids. Or release may be due to degradation of the carrier by contact with, for example, oral fluids. In some cases, the binder or carrier may evaporate upon application to the layer to the surface leaving the agent behind. In these cases, the agent may be released in a similar fashion as when the agent is directly attached to the surface, as described above. It may be appreciated that any suitable agent, such as fluoride materials, antibiotics or other drugs or medications, vitamins, bleaching materials, and/or breath fresheners, may be delivered to the oral environment in this manner.

In another embodiment, the agent is encapsulated or suspended in the layer. A common material for suspension of an agent is a semisolid material, such as a gel, jelly, or putty. Such a material may be applied to a surface of the shell by spraying, painting, and/or dipping to form a coating or film. Here, as in all cases, suspension is not limited to a scientific definition and may refer to any situation in which a carrier holds, contains, supports, or otherwise includes an agent. Alternatively or in addition, the semisolid material may be deposited in the cavities of the polymer shell which are shaped to receive the teeth. The cavities may be filled to any desired level. When the repositioning appliance is positioned over the teeth, the teeth will directly contact the semisolid material in the cavities and displace any extra material as the teeth are inserted into the cavities. Therefore, it is desired to fill the cavities to a level which will avoid excess overflow of the material from the appliance. Delivery of an agent by use of a semisolid suspension material is common in bleaching treatments and fluoride treatments, for example. However, such treatments apply the material with the use of a tray or generic appliance which does not apply repositioning forces to the teeth. By modifying a repositioning appliance, as described above, orthodontic treatment may continue throughout the delivery of such agents. It may be appreciated that any agent, particularly fluoride materials, antibiotics, bleaching materials, and breath fresheners, may be delivered to the oral environment in this manner.

Another common material for encapsulation or suspension of an agent is a controlled-release material. Thus, the layer may be of a rate-controlling material wherein the rate controlling material controls the rate at which the agent is released from the layer. Controlled-release or rate-controlled materials deliver a predetermined amount of an agent at a predetermined rate. Often such delivery maintains a steady-state concentration of an agent in an environment within a desired therapeutic range for a prolonged period of time. Thus, a prescribed dosage may be delivered. In addition, the ability to sustain delivery eliminates the need for repeated applications of the agent for dosed delivery to the oral environment.

Although such controlled release materials may be provided as a semisolid material, such as a gel, jelly, or putty, as described above, these materials may also be provided as a solid material which is attached to the polymeric shell of the repositioning appliance. One type of controlled-release material includes a polymer matrix membrane within which finely dispersed particles of an agent are suspended. The agent may diffuse through the matrix membrane according to a concentration gradient. Alternatively or in addition, the agent may be released by degradation of the polymer matrix membrane material. In either case, the controlled-release material may be provided as a sheet which may be laminated to a surface of the shell. The controlled-release sheet may be layered with the elastomeric polymer and vacuum formed over a mold to form the repositioning appliance. The controlled-release material may be arranged so that it is present on the inside or outside surfaces of the appliance depending on the material and desired application. Or, the controlled-release sheet may be laminated or bonded to a surface of the polymeric shell after forming to supply agent delivery in desired areas. Alternatively, the controlled-release material may be provided as a tablet or similar mass which may be inserted into the polymeric shell of the repositioning appliance. The agent may then elute from the tablet into the oral environment over time.

In another embodiment, the agent may be held within pores of a material and may elute out at a controlled rate from the pores. The agent itself may be absorbed into the pores of the material, or the agent may be suspended in a carrier which is absorbed into the pores of the material. In the latter case, the agent may be released from the carrier by diffusion and/or by controlled degradation of the carrier material. This may incorporate a rate-controlling mechanism in addition to the controlled-release of the agent from the pores. As mentioned, in some cases, enzymes in the patient's oral fluids will activate the release or degrade the carrier material to release the agent. It may be appreciated that the agent may be released by a combination of any of the release methods.

In a further embodiment, the polymeric shell of the repositioning appliance itself includes a controlled-release material containing the agent. In this case, at least a portion of a polymeric shell is formed from a controlled release material wherein the rate controlling material controls the rate at which the agent is released from the shell. As previously described, the controlled-release material may be a provided in the form of a sheet. Thus, the sheet of controlled-release material may be vacuum formed over a mold of the patient's teeth to form a repositioning appliance itself. In this manner, no additional elastomeric materials may be needed to form the appliance. The controlled-release material may be a polymer matrix membrane, a porous material, or any suitable material. Controlled-release may be designed so that the elution rate of the agent corresponds to the repositioning rate of the teeth. The agent may elute throughout the repositioning process, concluding as the teeth reach the desired arrangement prescribed by the appliance.

In a still further embodiment, the releasing mechanism coupled to at least some of the repositioning appliances includes a reservoir formed in the shell of the appliance in addition to the cavity which receives the teeth. Typically, a rate controlling membrane is disposed over the reservoir wherein the rate controlling membrane controls the rate at which the substance is released from the reservoir. The reservoir may be pre-filled or pre-loaded with an agent or substance for delivery. In this case, the appliance may be ready for insertion or use upon removal from any packaging without the need of loading the appliance with the agent for delivery. If the releasing mechanism is designed for a single delivery period, the appliance may be worn throughout the prescribed repositioning period and then disposed of. If the releasing mechanism is designed for multiple delivery periods, the reservoir may be replenished with the agent to be released any number of times throughout the prescribed repositioning period. It may be appreciated that any agent, particularly fluoride materials, antibiotics, bleaching materials, and breath fresheners, may be delivered to the oral environment in this manner.

In some instances, it may be desirable to change a visual characteristic of the polymeric shell of an oral appliance. Such appliances include a polymeric shell having a cavity shaped to be removably placeable over the teeth and a material on or within the shell that changes a visual characteristic of the shell. Such a change is typically in response to a change in the environment. In some cases, the visual characteristic is a color, such as green, red, or blue. Thus, the appliance may appear colored or a particular color under certain environmental conditions, either in the oral environment or when removed. The described material may be a dye which changes color in response to a change in temperature. For example, the dye may change color when the appliance is removed from the mouth and changes temperature from body temperature (37 degree C.) to room temperature (25 degree C.). Similarly, the dye may change color when the appliance is rinsed with cool water.

The appliance can be used to provide an intra-oral drug delivery system. In addition to the agents described above, other compounds can be used as well. For example, a drug coated appliance can be used to deliver desensitizing medication to sensitive teeth. The drug substance can simply be a small amount of the active ingredient in a desensitizing toothpaste or gel, such as Sensodyne®. The desensitizing agent is dispersed throughout the surface of the appliance and is delivered, at a substantially constant rate, to the patient's sensitive teeth for a relatively extended period of time.

Although the appliance may be pre-loaded with the agent and ready for use upon removal from any packaging, appliances that are not pre-filled or pre-loaded may require loading prior or immediately prior to placing the appliance over the teeth. Loading may include placing the agent in a teeth-receiving cavity. As described previously, the cavities may be filled to any desired level. When the appliance is positioned over the teeth, the teeth will directly contact the agent in the cavities as the teeth are inserted into the cavities. Alternatively, loading may include placing the agent into an agent release reservoir in the appliance immediately prior to placing the appliance over the teeth. The agent will then elute from the reservoir into the oral environment when the appliance is in place over the teeth. The elution rate may be controlled by a controlled release membrane which separates the reservoir from the surrounding environment. Loading may also include adhering a rate controlling material containing the agent to a surface of the appliance prior to placing the appliance over the teeth. Such a material may include a polymer matrix membrane which may be removably or permanently adhered to the polymeric shell of the appliance in desired areas for delivery of the agent. And finally, loading may include absorbing the agent into a porous material on or within the appliance immediately prior to placing the appliance over the teeth.

Mechanisms for releasing the agent may include a number of embodiments, including any such mechanisms previously described. Typically, mechanisms for releasing the agent includes a layer including the agent, as previously described, and coupling includes adhering the layer to at least a portion of a surface of the appliance. When the layer consists essentially of the agent, adhering may involve coating, spraying, dipping, or painting the agent on the surface of the appliance. Thus, a pre-formed appliance may simply be coated with the agent prior to insertion in the patient's mouth. When the layer includes an agent present in or on a carrier or binder, adhering may involve attaching the carrier or binder a surface of the appliance. Similarly, when the agent is encapsulated in the layer, the layer may be attached to the surface of the appliance. The layer may include a sheet of rate controlling material wherein the rate controlling material controls the rate at which the agent is released from the layer. In this case, the sheet may be bonded to the surface of the appliance with an adhesive. Alternatively, the sheet may be attached to the surface by press fitting. The sheet and the surface may each be shaped so that they snap or fit together by pressing them together. For example, the sheet may have a formed protrusion and the surface a formed inset, wherein the protrusion fits into the inset when pressed upon the inset and holds the sheet in place. In many instances, the appliance may be porous or have a reservoir which can be loaded with a desired agent at any time the treating professional and/or the patient decide that it is appropriate. For example, an appliance can be immersed in a solution of the agent, allowing the appliance to absorb or adsorb the agent at a particular time.

In addition, the sheet may be pre-formed to a shape adapted for fitting against the surface of the appliance or a surface of the teeth or gingiva. For example, the sheet may be pre-formed to reflect the shape of the surface of one or more teeth or the gingiva, particularly along the gingival margin. The preformed sheet may then be held against that surface when the sheet is coupled to the appliance and the appliance is placed over the teeth. Coupling may involve any mechanism of attaching the sheet to the appliance. In particular, the pre-formed sheet may further include an adhesive layer which may provide bonding of the sheet to the surface of the appliance.

The material to make to the appliance of FIG. 1 can be supplemented with additional fillers such as electrically conducting fillers, magnetic fillers, illuminating fillers, piezoelectric fillers, and/or light sensitive fillers. The material properties of the appliance made with or without these additional fillers such as modulus, electrical resistance, material permeability, and birefringence (degree of orientation of the material or stress), illuminating patterns or patterns under special light sources may change after the appliance is worn over time, as these properties are altered due to changes in structure, organization, and/or spatial spacing between the fillers. For example, it is well established that electrical conductivity of filled composites scales with filler volume concentration according to percolation theory. Therefore, mechanical deformation or thermal expansion of the non-conductive polymer matrix will lead to increased average inter-filler spacing, or decreased filler volume concentration, and consequently decreased electrical conductivity. Examples of electrically conductive fillers include metals, graphite, electrically conductive polymers, semiconductors, and superconductors. These changes in properties can be used as an indicator for compliance and can be diagnosed by instrumentation. Similarly, separation of conductive fillers will also lower thermal conductivity, which can also be measured by instrumentations. If the fillers have magnetic behavior in the presence of external stimulation, such as diamagnetics (Cu, Au, Ag, etc.) and paramagnetics (e.g. Al, Cr, Na, Ti, Zr, etc.); or exhibit intrinsic magnetic properties, such as ferromagnetics (Fe, Co, Ni, etc.), antiferromagnetics (e.g. MnO), and ferromagnetics (MFe$_2$O$_4$), then separation of the filler spacing due to mechanical deformation of the polymer matrix can also lead to decreases in magnetic properties above the Curie temperature. Mechanical deformation of composites with illuminating fillers, such as those that exhibit luminescence, fluorescence, or phosphorescence, will result in decreased illumination intensity. Bending deformation or displacement of piezoelectric fibers can result in electrical potentials which can be either measured, or used to activate other electrically driven indicators (e.g. low power LED light). Fillers with optical properties which depend on external electric field, for example those that shift their absorption coefficients in the UV, IR, or visible spectrum can also serve as indicator of matrix deformation.

Figure 2A:
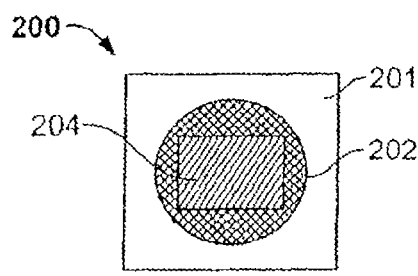
FIGS. 2A-2C show a first embodiment of the compliance indicator of FIG. 1.

Referring now to FIG. 2A, an embodiment of an indication attachment device 200 is shown. The indication attachment device 200 includes a polymer well 201, and the well 201 includes a semi-permeable membrane 202. The membrane 202 allows a two-way flow between the well 201 and an interface to the oral environment. Within the well 201, a material 204 such as a dyed material is provided.

In some embodiments, the dyed material 204 is a releasable material, such as dyed poly(vinylsiloxane) (PVS) material. The PVS material is used to hold the dye, and the membrane 202 can be a cellulose acetate membrane. Those skilled in the art will understand that other releasable materials such as polyether, polyurethane, ethyl vinyl acetate can also be manipulated to result in the teachings of this patent.

In another embodiment, the well material 204 can be an enzyme or a reactor that reacts with enzymes from the oral fluids. When oral fluids or enzyme from the oral fluids enters the well, the material 204 reacts with the enzyme to provide an indication. Alternatively, a pH indicator can be used as the material 204. In yet another embodiment, the membrane 202 can be silicon instead of PVS.

In another embodiment, the polymer can be water-soluble polymer that includes water-soluble polymers, lightly crosslinked hydrogels, and high molecular weight with hydrogen bonding plastics that demonstrate some limited water resistance. Natural-based water-soluble polymers include starch, starch-oxided, cellulose, cellulose-alkoxylated, cellulose-carboxyalkylated, chitin, chitosan, pectins, hyaluronic acid, proteins, and lignin. Water-soluble polymers can also be created from synthetic raw material through polymerization by addition/vinyl, condensation, and ring-opening. Examples of these types of polymers are poly(vinyl alcohol), polyesters, and poly(alkylene oxides). The hydrolytic instability of biodegradable polymers is advantageous because the presence of the oral fluids will facilitate the degradation of the polymer.

Figure 2B:
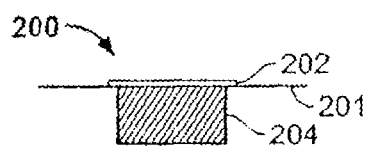
Figure 2C:
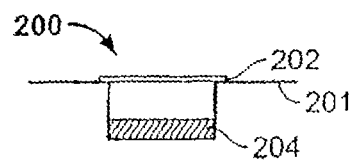

Referring now to FIG. 2B, a cross-sectional view of the compliance indication attachment device (compliance indicator) 200 is shown. As viewed therein, the membrane 202 is positioned above the polymer well, chamber, or housing 201 with the releasable material and or dye 204 enclosed therein. As shown in FIG. 2C, after a predetermined period of time, for example two weeks, a portion of the dyed PVS material 204 has seeped out causing a change in appearance of the indication attachment device. The dye is released while the PVS stays inside the device. In this case, a color change can occur or alternatively, the volume of the material has changed, in this case it has reduced in size.

In some embodiments, the compliance indicator 200 has a clear, tooth-colored, or esthetically pleasing polymer reservoir well, chamber, or housing 201. A transparent or translucent semi-permeable membrane 202 separates the content within the reservoir chamber 201 from the external oral environment. The content(s) within the reservoir chamber 201 depends on the overall strategy to monitor compliance. In one implementation, contents diffuse out from the reservoir chamber 201, through the membrane 202, into the external environment. For example: the content can be an FDA approved visible dye which diffuses from the chamber 201, through the membrane 202, and into the external oral environment. When the content is emptied, the content color diminishes in brightness and value. Colorants that are permitted for direct addition to human food by the US FDA include annatto extract, beta-carotene, beet powder, canthaxanthin, caramel color, carrot oil, cochineal extract (carmine); cottonseed flour, fruit juice, paprika, riboflavin, saffron, turmeric, vegetable juice, FD&C Blue No. 1 (brilliant blue) and No. 2 (indigotine), FD&C Green No. 3 (fast green FCF), FD&C Red No. 3 (erythrosine) and No. 40 (allura red), FD&C Yellow No. 5 (tartrazine) and No. 6 (sunset yellow). Other food colorants such as those found at FDA's Center for Food Safety and Applied Nutrition website: http://www.cfsan.fda.gov/.about.dms/col-toc.html can be used as well.

In another implementation, matter from the external environment diffuse in, and reacts with the contents 204 within the reservoir chamber 201. For example, glucose molecules from the external environment diffuse through the membrane 202, and reacts with enzymes inside the content and the resultant enzymatic products interact with other reactants inside the content to cause color change. As more glucose molecules diffuse in, content color increases in brightness and value. A convenient enzyme system is glucose oxidase and horseradish peroxidase. The first enzyme, glucose oxidase, catalyzes the oxidation of glucose to form gluconic acid and hydrogen peroxide. Hydrogen peroxide then reacts with 3-3,5,5'-tetramethylbenzidine (TMB) under catalytic action of horseradish peroxidase to convert yellow TMB to green. Other colorants, such as potassium iodide (green to brown) may also be used. These enzymes can be immobilized within the chamber. The rate of reaction, and hence color change, can be controlled by selecting the permeability of the membrane 202, the concentration of reactants inside the chamber 201, and the method of delivery. The rate of reaction or concentration of the glucose molecules can also be detected through spectroscopy or other analytical testing. Test results will correlate with compliance to treatment.

Figure 3A:
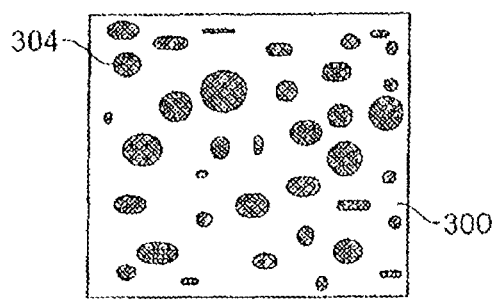
FIGS. 3A-3B show a second embodiment of the compliance indicator of FIG. 1.
Figure 3B:
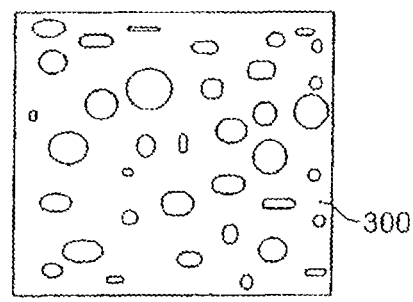

Referring now to FIGS. 3A and 3B, another embodiment of an indication attachment device is shown. In the embodiment of FIG. 3A, a porous polymer material is provided on a sheet 300. The polymer material is disposed on the sheet 300 as one or more containers 304. The container 304 may be a well as disclosed above in the discussion of FIGS. 2A-2C. After a predetermined period of usage, the polymer material changes appearance, for instance, changes either to the color or the size as shown in FIGS. 2B-2C. Other implementations can include colored polymers (both thermoplastic and thermoset materials) and composites utilizing the same compliance mechanism as the porous polymer material.

The compliance indicator of FIGS. 3A-3B thus can be a dye encapsulated in a polymer which is released in the presence of oral fluids. The dye can be colorants that react with the oral fluids and that are released from the polymer. The polymer can be porous polymer such as monolithic porous polymer (currently used in chromatography), PVS, a high internal phase emulsion (HIPE polymer currently used in drug release), or any macroporous polymer. The dyed polymer will be constructed into a small button that can be bonded to the exterior of the aligner. The amount of dye loss will correspond with the amount of time the aligner was in use. The pore size of the polymer and the particle size of the dye will affect the rate of diffusion of dye from the button to the oral fluids environment and depending on compliance needs, these factors can be controlled.

Porous polymers are prepared by adding "porogens" during the polymerization process of resins. Porogens are soluble in the monomer but insoluble in formed polymers. As polymerization occurs, pores are formed in the spaces where porogens are found. The newest type of porous polymers is known as "high internal phase emulsions" ("HIPE"). HIPE structures have pore diameters much larger than previous porous materials which had only pore diameters in the angstroms.

Another porous polymer is the monolithic porous polymer currently being used in chromatography. The polymerization of this rigid macroporous polymer takes the shape of the mold, usually a column, into which the monomers and porogens are poured into. Generally, the pore volume is nearly equal to the amount of porogens added into the monoliths.

Figure 4A:
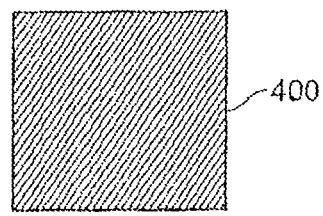
FIGS. 4A-4B show a third embodiment of the compliance indicator.
Figure 4B:

Referring now to FIGS. 4A and 4B, a button embodiment of an indication attachment device 400 is shown. In this embodiment, a biodegradable polymer material is attached to either a tooth or a dental appliance. After a certain period of use, the polymer material either changes shape or size or color, and as shown in FIG. 4B, the volume of the biodegradable polymer material is subsequently reduced. In some embodiments, the button is a biodegradable polymer button. The button can be molded from a biodegradable polymer and bonded to the exterior of the aligner. The button will have a predetermined degradation period such as a two week degradation period in the constant presence of oral fluids. Potentially the polymer can be colored for a more visible indication of the degradation of the button. The size and material will determine the degradation period of the button. However, other factors such as brushing of the aligner and rinsing will have to be taken into consideration when determining the optimal degradation time of the button.

The degradation products often define the biocompatibility of a polymer. Synthetic biodegradable polymers are favored over natural ones because of reliability of raw materials. The following is a list of common biodegradable polymers: polyglycolide (PGA), polylactide (PLA), 1-lactide (LPLA), poly(dl-lactide) (DLPLA), poly(.epsilon.-caprolactone) (PCL), polydioxanone (PDO), poly(glycolide-co-trimethylene carbonate) (PGA-TMC), and polyorthoesters.

Figure 5:
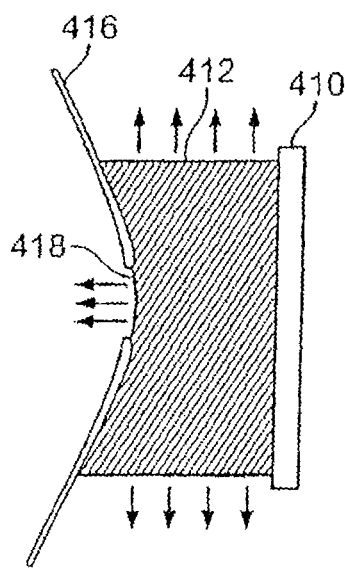
FIG. 5 shows a fourth embodiment of the compliance indicator.

FIG. 5 shows yet another embodiment of an indication attachment device. In this embodiment, an appliance 416 receives an adhesive dye matrix 412. The matrix 412 is sealed either at one end or both ends using a backing film 410. The material in the matrix 412 can be released on the sides between the appliance 416 and the film 410 or between the two backing films. An opening 418 may be provided in the appliance 416 and one side of the backing film to facilitate dye release. In one implementation, a transdermal patch may be applied in a manner similar to drug releasing transdermal patches. Instead of embedding and releasing drug in the adhesive matrix, a dye is released and the mechanism for dye loss is moisture (oral fluids). In one implementation, appliance wear compliance is indicated by the color of the adhesive layer: the more dye lost, the longer the wear time.

Figure 6:
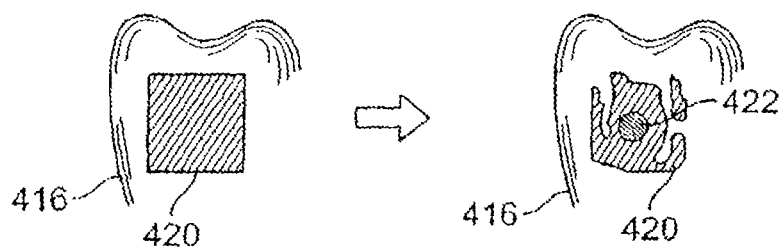
FIG. 6 shows a fifth embodiment of the compliance indicator.

FIG. 6 shows yet another embodiment where the wear indication is achieved through a water dissolvable film. In this embodiment, an opaque water soluble film 420 is positioned to cover one or more colored areas, regions, spots, or dots 422 on an appliance or on a tooth. The film can be a protective coating that can be used to protect the indicator (e.g., dot) from wear, such as from brushing teeth, etc. Since these appliances may be intended to be used for most of the day (e.g., 20+ hours), in many situations, protection of the indicator may be helpful in determining compliance.

In some embodiments, the protective coating can be removable and can be used to protect the indicators before and/or during application to an appliance or to one or more teeth. Such embodiments can also improve the accuracy of compliance analysis, in some instances.

In some embodiments, the dots 422 can be a series of colored dots with varying thicknesses of film 420 and each exposed color corresponds to a different amount of appliance wear time. In the embodiment where the dots 422 are imprinted on the appliance, the film 420 is layered onto the surface of the appliance. The mechanism of releasing dye is moisture (oral fluids).

Figure 7:
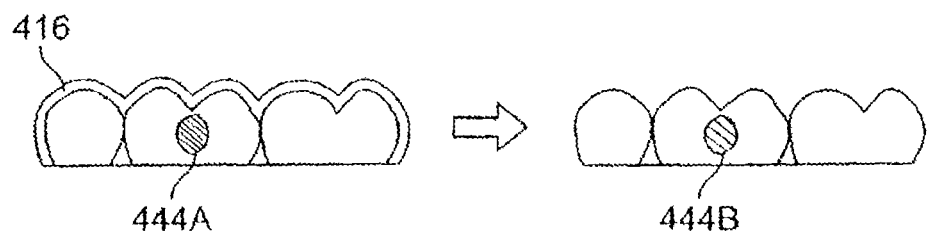
FIG. 7 shows a sixth embodiment of the compliance indicator.

FIG. 7 shows another embodiment where a tooth attachment 444A is made with a dye-releasing composite. The dye-releasing composite 444A bonded to a tooth will be covered by an appliance 416. Over time, the dye-releasing composite 444A has a reduced or no color loss compared to the loss for a dye on an uncovered tooth attachment 444B. The color of the attachment will correspond to the amount of aligner wear. The mechanism of dye releasing is moisture (oral fluids) in this embodiment.

In yet other implementations, a diagnostic indicator can be provided. The diagnostic indicator is similar in device construction to the compliance indicator, and utilizes the inwards diffusion strategy, where biochemical analytes from the external environment are allowed to diffuse through the membrane to react with the contents within the reservoir chamber. Thus, biomarkers from the external environment diffuse through the membrane, and react with reagents inside the content to directly or indirectly induce color change or chemical change that can be quantified through human eye or laboratory testing or computerized vision systems. As more biomarkers diffuse into the diagnostic indicator, the content color changes, for example increases in brightness and value. Possible biomarkers include enzymes, pH, glucose, salt, oral film, plaque, microorganisms that may exist in the oral cavity and amount of oral fluids.

Figure 8:
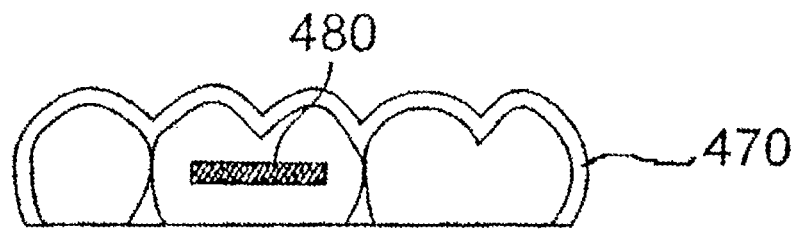
FIG. 8 shows a seventh embodiment of the compliance indicator.

In the embodiment shown in FIG. 8, the compliance indicator can be a time temperature indicator 480. The indicator 480 is intra-orally placed in the mouth (either directly on a tooth or on an appliance 470) and provides an indication of the time the indicator has been at a preselected intra-oral temperature environment.

Figure 9:
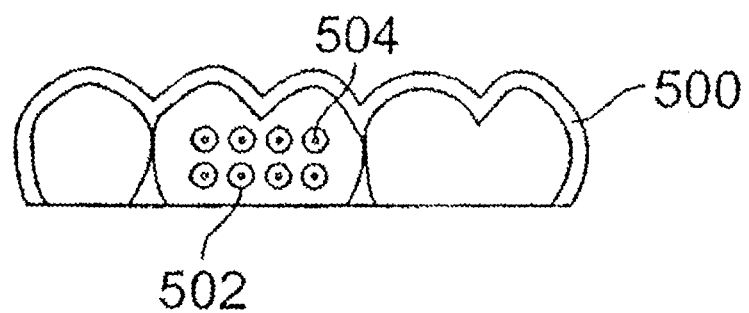
FIG. 9 shows an eighth embodiment of the compliance indicator.

In yet another embodiment shown in FIG. 9, a plurality of brushes 502 having a colored fiber 504 is positioned on the appliance 500. As the brush 502 is gradually eroded by wearing the appliance 500, a dye, or other suitable indicia of wear in the fiber 504 is exposed for visual detection by a human or by a machine. Alternatively, the brushes 502 can be placed on one or more teeth instead of on the appliance 500.

In yet another embodiment, the compliance indication is human readable by changing physical or mechanical or visual properties that are readily observable by a human. In other embodiment, the compliance indication is machine readable. For instance, in one embodiment that alters the electrical characteristics of an appliance during wearing of the appliance, an electrical measurement can be made by a computer for detecting compliance. In another embodiment that uses biomarkers, a computer with biomarker sensor can be used with suitable computer program to detect compliance. In yet another embodiment, a color change can be detected by a computer vision program to detect compliance.

Each computer program is tangibly stored in a machine-readable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

Portions of the system and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission, or display devices.

Figure 10:
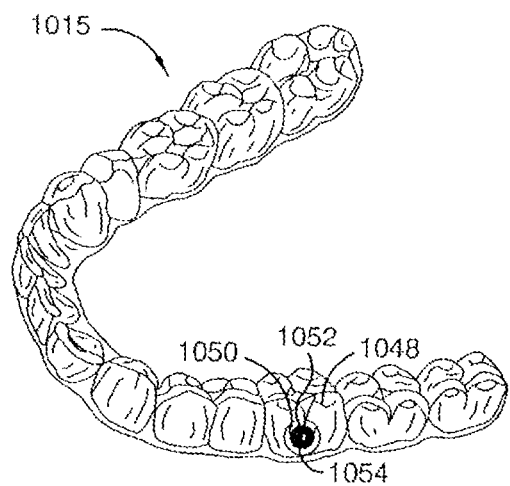
FIG. 10 shows an appliance having a release agent receptacle according to an embodiment of the prevent disclosure.

FIG. 10 shows an appliance having a release agent receptacle according to an embodiment of the prevent disclosure. FIG. 10 illustrates that a release agent receptacle can be provided (e.g., placed on, manufactured on) on an appliance 1015 such as an aligner for dental treatment, among other types of dental appliances.

In the embodiment of FIG. 10, the release agent receptacle includes an outer portion 1050 provided on appliance surface 1048, with an inner portion 1052 provided within the outer portion 1050, and an aperture 1054. In some embodiments, the inner portion 1052 can be encapsulated within the outer portion 1050.

In various embodiments, an outer portion can, for example, be provided by a polymer and/or curable material (e.g., ultra violet-curable acrylic) among other types of suitable materials. Other examples of suitable materials include, but are not limited to materials such as an ultra violet-acrylic material, an epoxy material, a urethane material, a rubber material, an ethylene vinyl acetate material, an elastomer material, a plastic material, and/or a silicone material, among other suitable material types.

The inner portion 1052 can be utilized as an active portion of the release agent receptacle, wherein the inner portion has an active ingredient such as a dye, pigment, or other indicator material and/or materials that can be used for treatment. In such embodiments, these receptacles can be referred to as compliance indicators so long as they have the functionality of compliance indication.

In some embodiments, the active ingredient can be embedded in a polymer or other suitable type of material. Polymers and other such materials can be useful in such embodiments, for example, because the rate at which the active ingredient is released or leaches out may be controlled by the type of polymer or other such material the active ingredient is embedded in.

In order to facilitate the release of the material in the inner portion of the release agent receptacle, one or more apertures 1054 can be provided through the outer portion 1050 and to the surface of the inner portion 1052. In some embodiments, the aperture 1054 can be provided through the outer portion 1050, through some or all of the inner portion 1052 and/or into or through the outer portion 1050 that is proximate to the surface 1048 of the appliance 1015. In various embodiments, the size and/or shape of the one or more apertures can be adjusted to change the amount, speed, direction, and/or other characteristics of the release of the material from the inner portion 1052.

The one or more apertures can be formed in any suitable manner. For example, in some embodiments, the aperture can be drilled through the cured adhesive to allow moisture, more specifically saliva, to interact with an active ingredient in the inner portion. In some embodiments, the aperture can be formed during the formation of the other portions of the appliance (e.g., in some embodiments where the appliance and release agent receptacle are formed integrally).

The active ingredient can be any suitable ingredient for use in oral indication, diagnosis, and/or treatment and can be released in any suitable manner. For example, in some embodiments, the mechanism of dissolution of the active material and release can be through moisture from the mouth of the patient. A suitable example of an active ingredient is FD&C blue dye in the case of the compliance indicator, however, such and example should not be viewed as limiting on the embodiments of the present disclosure.

Figure 11:
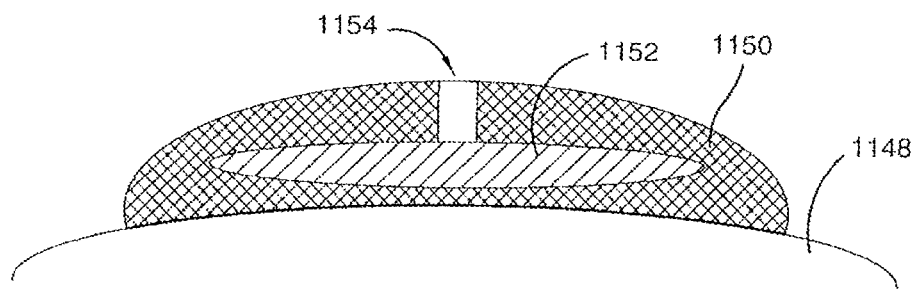
FIG. 11 shows a cut-away side perspective view of the receptacle embodiment of FIG. 10.

In some embodiments, as illustrated in FIG. 11, the release agent receptacle can be formed with or integrally bonded to the surface of the appliance. In some embodiments, the release agent receptacle can be adhered to or non-integrally bonded to the surface of the appliance.

In such embodiments, a bonding material can be utilized that can, for example, be composed of a biocompatible pressure-sensitive adhesive (e.g., acrylic, silicone, and/or polyisobutene) which can allow for adhesion of the release agent receptacle to the aligner surface, or other suitable surfaces.

In some embodiments, the compliance indicator can be a wear indicator. As discussed herein, use of various materials can be utilized to provide a number of different wear rates. A wear material can, for example, be composed of a water-soluble polymer (e.g., high molecular weight polyvinyl alcohol) mixed with a FD&C (FDA certified) "aluminum lakes" dye which allows for leaching of the color over a period of time, among other materials Although the wear rates of these indicators may not be standardized from one patient to another, the wear rates of these indicators can be predetermined with respect to each other. In such embodiments, indicators of various wear rates with respect to each other can be utilized.

Such wear indicators can be used as compliance indicators or as treatment disbursement apparatuses (e.g., for the disbursement of agents as described herein) as the wearable material wears during use of the appliance to which it is associated. This wear can, for example be produced through interaction with moisture as discussed above.

Such wear rates can be established, for example, by exposing the wear indicator to a uniform reactant (e.g., a material that causes the indicator to change). The periods of change to the indicators can be measured and can, therefore, be used to set the amount of expected change with respect to the other indicators similarly tested.

For instance, a dye may have a particular wear pattern over time, which may be uniform or may increase, decrease, or otherwise change over time. Such rates can be determined and the usage of the appliance calculated based upon where the wear indication provided by the indicator is on the wear pattern of the particular material being used in the indicator.

Some examples of the type of wear that can be used to determine the wear rate of the wear layer can determined based upon one of the factors selected from the group including amount of saliva produced, one or more tooth anatomies or locations, a composition of saliva, an analysis of sleep habits of a patient, an amount of liquid consumption, and one or more types of liquid consumed, among other criteria. The analysis of compliance can be accomplished in any suitable manner based upon the information provided by the initial indicators.

FIG. 11 shows a cut-away side perspective view of the release agent receptacle embodiment of FIG. 10. In the embodiment of FIG. 11, the release agent receptacle includes an outer portion 1150 provided on appliance surface 1148, with an inner portion 1152 provided within the outer portion 1150, and an aperture 1154. In some embodiments, the inner portion 1152 can be encapsulated within the outer portion 1150 with the aperture being formed after the encapsulation has been done.

In some embodiments, the appliance 1148 can include one or more of the release agent receptacles mounted on the appliance 1148 to indicate compliance and/or the amount of treatment disbursement that has been done by demonstrating a change in at least one characteristic of the release agent receptacle. The changed characteristic can, for example, be a color, shape, and/or size, among others. In some embodiments, compliance and/or disbursement can be indicated by an absence of a change.

In order to facilitate the release of the material in the inner portion of the release agent receptacle, one or more apertures 1154, as discussed above, can be provided through the outer portion 1150 and to the surface of the inner portion 1152. In some embodiments, the aperture 1154 can be provided through the outer portion 1150, through some or all of the inner portion 1152, and/or into or through the outer portion 1150 that is proximate to the surface 1148 of the appliance 1115.

Some embodiments may also continue the aperture through a portion or all of the thickness of the appliance. Such embodiments may allow for material from the inner portion 1152 to interact with the teeth and/or gingiva of the patient that are positioned on or near the aperture 1154 within the appliance 1115. In various embodiments, the size and/or shape of the one or more apertures can be adjusted to change the amount, speed, direction, and/or other characteristics of the release of the material from the inner portion 1152.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow. For example, although films or appliances have been disclosed as mechanisms for compliance measurement, droplets can be used to deliver the compliance indicating substances to the patient as well.

Other embodiments for compliance indication can be used as well. Whereas particular embodiments of the present invention have been described herein for purposes of illustration, it will be evident to those skilled in the art that numerous variations of the details may be made without departing from the invention as defined in the appended claims.

We claim:

1. A dental appliance, comprising:
   a shell having a plurality of tooth-receiving cavities shaped to receive and resiliently reposition teeth in a patient's mouth from a first arrangement toward a second arrangement; and
   a usage indicator on the shell, the usage indicator including a reservoir encapsulated within an outer portion, the reservoir comprising an agent configured to react with an enzyme within liquid contents within the patient's mouth to cause a change in color of the usage indicator, wherein the outer portion includes:
      a bottom layer between the shell and the agent within the reservoir; and
      a top layer covering the agent, the top layer configured to control exposure of the agent to the liquid contents, wherein the usage indicator provides a visual estimation of an amount of time that the dental appliance has been in the patient's mouth based on the change in color of the usage indicator.

2. The dental appliance of claim 1, wherein the dental appliance is a removable appliance adapted to fit over the patient's teeth.

3. The dental appliance of claim 1, wherein the usage indicator is on an outer surface of the shell.

4. The dental appliance of claim 1, wherein the usage indicator is made of an elastomeric polymer.

5. The dental appliance of claim 1, wherein the top layer includes an aperture that allows passage of the liquid contents from outside of the usage indicator to contact and activate the agent.

6. The dental appliance of claim 1, wherein the top layer is transparent or semi-transparent.

7. The dental appliance of claim 1, wherein the top layer is configured to control release of activated agent from the reservoir.

8. The dental appliance of claim 1, wherein reaction of the agent with the enzyme produces a product that interacts with a reactant within the reservoir to cause the change in color.

9. A dental appliance comprising:
   a shell having a plurality of tooth-receiving cavities shaped to receive and resiliently reposition teeth in a patient's mouth from a first arrangement toward a second arrangement; and
   a usage indicator on the shell, the usage indicator including a reservoir encapsulated within an outer portion, the reservoir comprising an agent that comprises an enzyme configured to react with molecules within oral fluid within the patient's mouth to cause a change in color of the usage indicator, wherein the outer portion includes:
      a bottom layer; and
      a top layer covering the agent and including an aperture that allows passage of the oral fluid from outside of the usage indicator to contact the agent and activate the agent, wherein the change in color of the usage indicator provides a visual estimation of an amount of time that the dental appliance has been in the patient's mouth.

10. The dental appliance of claim 9, wherein the usage indicator is on an outer surface of the shell.

11. The dental appliance of claim 9, wherein the usage indicator is on a buccal side of the shell.

12. The dental appliance of claim 9, wherein the top layer is made of an elastomeric polymer.

13. The dental appliance of claim 9, wherein the agent is held within a porous material or incorporated within a polymer material under the top layer.

14. The dental appliance of claim 9, wherein changing an amount of agent remaining under the top layer changes an appearance of the usage indicator.

15. The dental appliance of claim 9, wherein changing an amount of agent remaining under the top layer changes the color or a size of the usage indicator.

16. A method of forming a dental appliance having a usage indicator, the method comprising:
   forming the dental appliance for fitting on a patient's teeth, the dental appliance including a shell aligner having a plurality of tooth-receiving cavities shaped to receive and resiliently reposition the patient's teeth from a first arrangement toward a second arrangement; and
   forming the usage indicator on the shell aligner by encapsulating a reservoir within an outer portion of the usage indicator, wherein the outer portion includes:
      a bottom layer between the shell aligner and an agent within the reservoir, the agent configured to react with an enzyme within liquid contents within the patient's mouth to cause a change in color of the usage indicator; and
      a top layer covering the agent within the reservoir, the top layer configured to control exposure of the agent to the liquid contents within the patient's mouth, wherein the usage indicator provides an estimation of an amount of time that the dental appliance has been in the patient's mouth based on the change in color of the usage indicator.

17. The method of claim 16, wherein forming the usage indicator comprises forming an aperture within the top layer that allows passage of oral fluid from outside of the usage indicator to contact and activate the agent.

18. The method of claim 16, further comprising forming a series of shell aligners configured to progressively align the patient's teeth.

19. The method of claim 16, further comprising incorporating the agent within a porous material or a polymer material.

* * * * *